(12) United States Patent
Yamazaki (10) Patent No.: US 6,285,781 B1
(45) Date of Patent: *Sep. 4, 2001

(54) RADIOGRAPHIC APPARATUS AND METHOD

(75) Inventor: Tatsuya Yamazaki, Utsunomiya (JP)

(73) Assignee: Canon Kabushiki Kaisha, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 5 days.

(21) Appl. No.: 09/048,083

(22) Filed: Mar. 26, 1998

(30) Foreign Application Priority Data

Mar. 27, 1997 (JP) .................................................... 9-075496

(51) Int. Cl.⁷ ........................................................ G06K 9/00
(52) U.S. Cl. ................................................................ 382/132
(58) Field of Search ............................... 382/132, 129, 382/130, 131, 128, 275; 395/326; 358/400; 378/37, 62, 21, 70, 86, 87

(56) References Cited

U.S. PATENT DOCUMENTS

| | | | |
|---|---|---|---|
| 3,860,817 | * | 1/1975 | Carmean ............................ 250/320 |
| 4,382,184 | * | 5/1983 | Wernikoff ........................... 378/37 |
| 4,727,562 | | 2/1988 | Belanger ............................ 378/98.4 |
| 4,918,713 | * | 4/1990 | Honda ................................ 378/99 |
| 5,028,784 | * | 7/1991 | Arakawa et al. .................. 250/327.2 |
| 5,309,496 | * | 5/1994 | Winsor ............................... 378/98.2 |
| 5,465,284 | * | 11/1995 | Karellas ............................. 378/62 |

FOREIGN PATENT DOCUMENTS

| | | | |
|---|---|---|---|
| 0 142 864 A2 | 5/1985 | (EP) | ............................... A61B/6/00 |
| 0 386 587 | 9/1990 | (EP) | ............................... A61B/6/02 |

OTHER PUBLICATIONS

"Removing the anti–scatter in mammography" By R.P. Highnam, J.M. Brady and B.J. Shepstone ; Digital Mammography '96 pp. 459–462.*

* cited by examiner

Primary Examiner—Andrew W. Johns
Assistant Examiner—Shervin Nakhjavan
(74) Attorney, Agent, or Firm—Fitzpatrick, Cella, Harper & Scinto (57) ABSTRACT

A radiographic apparatus for obtaining the radiation image of an object has a phototaking portion for phototaking the radiation image of the object, the phototaking portion being capable of obtaining the data of the radiation image passed through a grid, and a signal processing portion for providing the data of the image of the grid expected when the object is present, the signal processing portion effecting the process of removing the data of the expected image of the grid from the data of the radiation image of the object passed through the grid obtained by said phototaking portion.

26 Claims, 6 Drawing Sheets

RADIOGRAPHIC APPARATUS AND METHOD

BACKGROUND OF THE INVENTION

1. Field of the Invention

This invention relates to a radiographic apparatus and a radiographic method for effecting phototaking by the use of radiation typified by X rays.

2. Related Background Art

Generally radiographic apparatuses are used in the fields of radiography for medical treatment, non-destructive radiography for industry, etc. Their form of use will hereinafter be described with reference to FIG. 1 of the accompanying drawings. When radiation radiated from a radiation source 1 is applied to an object 2, the radiation is intensity-modulated and scattered in conformity with the structure of the object by the mutual action (absorption, scattering, etc.) between the radiation and the object, and has its scattered rays removed by a grid 4, whereafter it arrives at a fluorescent material 5 as a radiation image. Generally, as the fluorescent material, use is made of an intensifying screen comprising $CaWO_4$ or $Gd_2O_2S:Tb$ applied to a back-up material or fluorescent material crystal such as CsI. The fluorescent material has a characteristic of emitting fluorescence of intensity proportional to the amount of applied radiation and therefore, the aforementioned radiation image is converted into a visible optical image in the fluorescent material 5. Image receiving means 6 is means for producing an image conforming to the quantity of received light, and the visible optical image produced in the fluorescent material is made into an image conforming to the quantity of light by the image receiving means 6. Generally in a radiographic apparatus, the image receiving means is film and a radiation image is recorded on the film as a latent image providing photographic density substantially proportional to the logarithm of the quantity of fluorescence, and is presented as a visible image after the developing process and is used for diagnosis or examination or the like.

Use has also begun to be made of a computed radiography apparatus using as a fluorescent material an imaging plate (hereinafter referred to as an IP, having applied thereto BaFBr:Eu fluorescent material and BaF:Eu fluorescent material, which are accelerated fluorescent materials. When secondary excitation is effected on the IP primarily excited by the application of radiation, by the use of visible light such as a red laser, emitted light called accelerated fluorescence is created. The computed radiography apparatus is an apparatus for detecting this emitted light by an optical sensor such as a photomultiplier to thereby phototake a radiation image.

Further, there has recently been developed a technique using as image receiving means a photoelectric conversion device comprising pixels comprising minute photoelectric conversion elements, switching elements or the like arranged in the form of a grid to obtain a digital image. There has also been developed a technique using a converting material for converting radiation into electrons, for example, amorphous selenium, CdTe or an ion chamber, and a detecting device for detecting electrons to obtain a digital image. As examples of the advantages of utilizing a radiation detecting device, the following items may be mentioned. First, an image can be directly obtained as digital data and therefore, image processing becomes easy and the correction of inappropriate phototaking conditions, the image emphasis of a concerned area, etc., easily become possible. Also, by using image communication means such as facsimile apparatus, it is possible for a medical specialist in a large hospital to effect a diagnosis to a patient in a remote place where there is no medical specialist. Also, if image digital data are stored in a magneto-optical disc or the like, the required preservation space can be remarkably decreased as compared with a case where film is stored. Also, images in the past can be easily searched for and therefore, it becomes possible to present a reference image easily as compared with a case where film is searched for.

Figure 1:
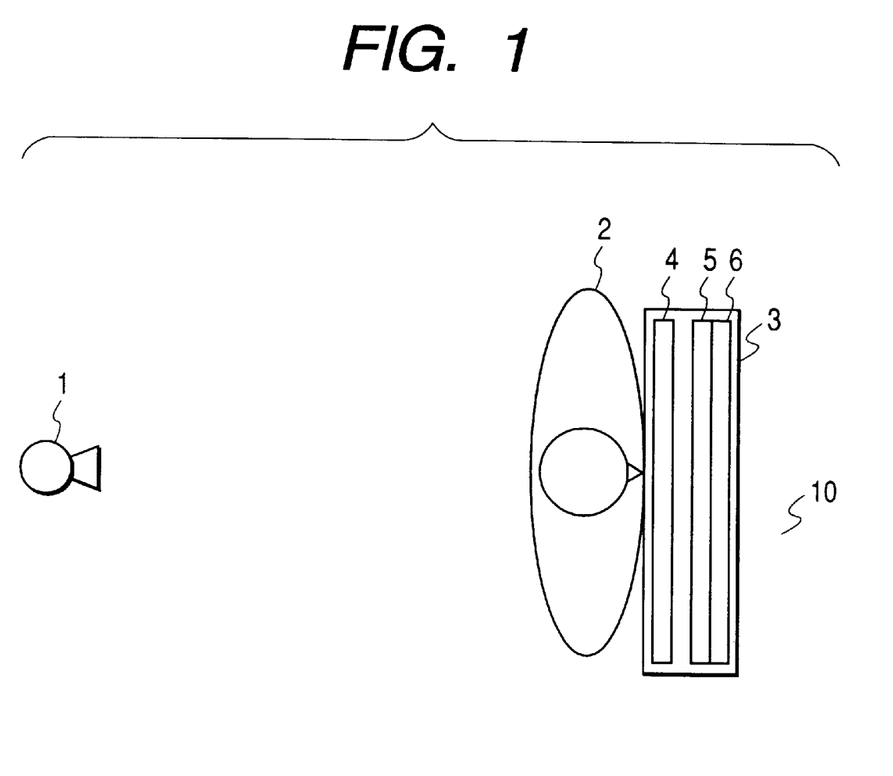
FIG. 1 illustrates a radiographic apparatus according to the prior art.

A grid will now be described briefly with reference to FIG. 1 of the accompanying drawings. A grid 4 is generally a plate in which a lamination comprising leaden plates and aluminum plates alternately laminated has been thinly cut out, and acts to bring the leaden plates arranged substantially in parallel with one another into coincidence with the direction of travel of primary radiation to thereby eliminate unnecessary scattered radiation created from an object 2, and improve the contrast of a radiation image. The radiation image of the grid is superposed on the radiation image of the object and is recorded on image receiving means 6, and the spatial frequency of the grid is suitably selected, so that the image of the grid will not hinder to diagnosis. Generally 3 to 6 lines/mm are selected as the spatial frequency of the grid, and the more is reduced the spatial frequency of the grid, the clearer the image of the grid looks, but doctors are considered to effect diagnoses without being misled by the image of the grid by training.

However, a conventional art radiographic apparatus using the aforedescribed photoelectric conversion device suffers from a problem which will be described below.

The mesh of the grid is modulated and phototaken by a radiation detecting device such as a photoelectric conversion device for effecting discrete sampling. According to the sampling theorem, discrete sampling means typified by the photoelectric conversion device cannot reproduce an input image of Nyquist frequency or higher. Therefore, if the image of the grid has a spatial frequency higher than the Nyquist frequency of the photoelectric conversion device, the image of the grid is spatial-frequency-modulated and intensity-modulated and is observed as Moire stripes. The output image at this time becomes like a striped pattern of a spatial frequency greater the original grid frequency is superposed, for example, on the radiation image of an object. On the other hand, even when the discrete sampling means is not used, there is a basic requirement for removing the image of the grid superposed on the image of the object.

SUMMARY OF THE INVENTION

It is an object of the present invention to provide a radiographic apparatus and a radiographic method for effectively and accurately removing the image of a grid superposed on the radiation image of an object in radiography using a radiation detecting device, and obtaining a radiation image excellent in image quality.

Other objects of the present invention will become apparent from the following description of some embodiments of the invention.

DESCRIPTION OF THE PREFERRED EMBODIMENTS

Figure 2:
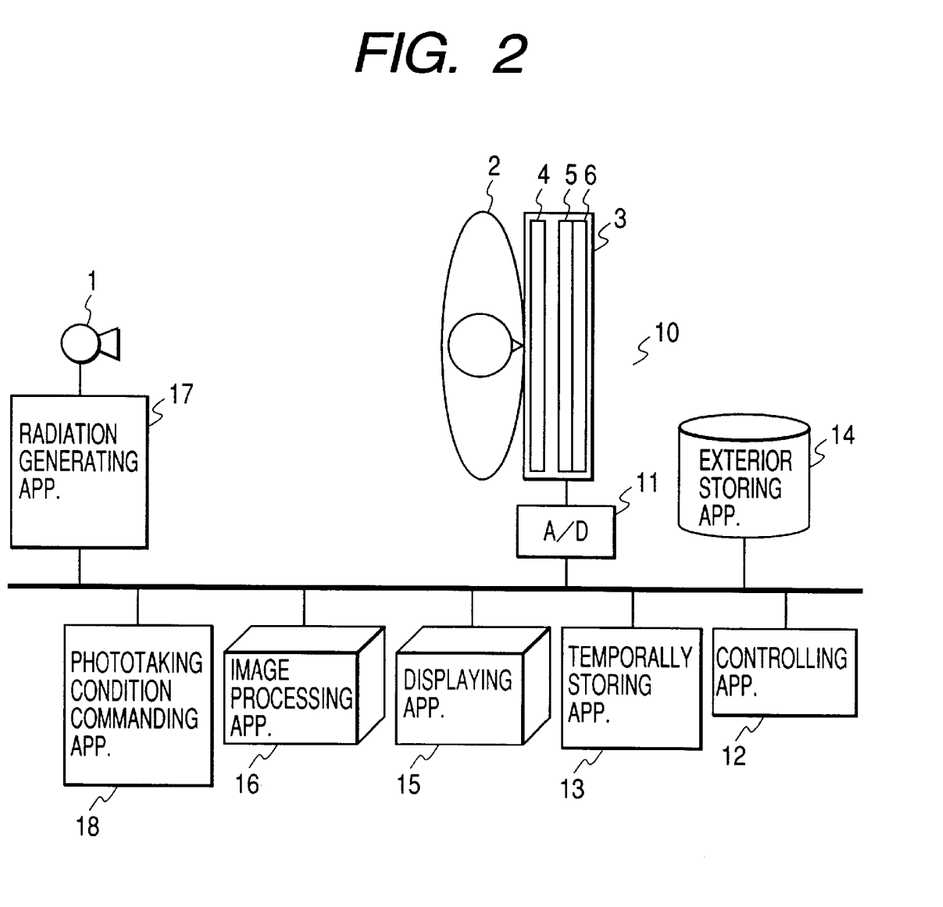
FIG. 2 illustrates a radiographic apparatus according to a first embodiment of the present invention.
Figure 3A:
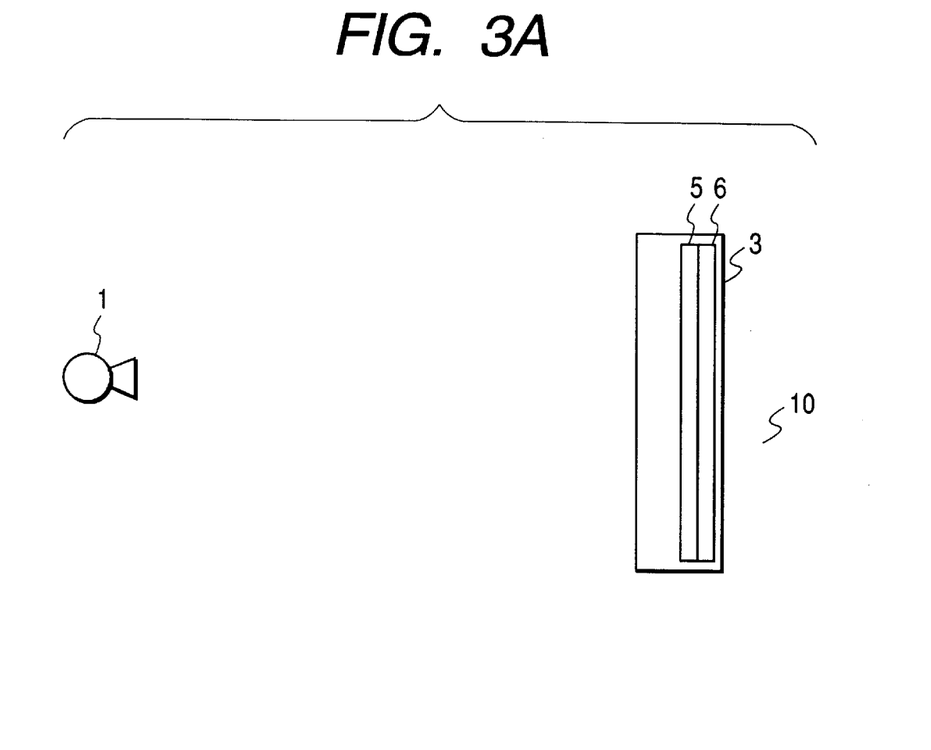
FIG. 3A illustrates a method of measuring the input and output characteristics of a radiation detecting device in a state in which a grid is absent.
Figure 3B:
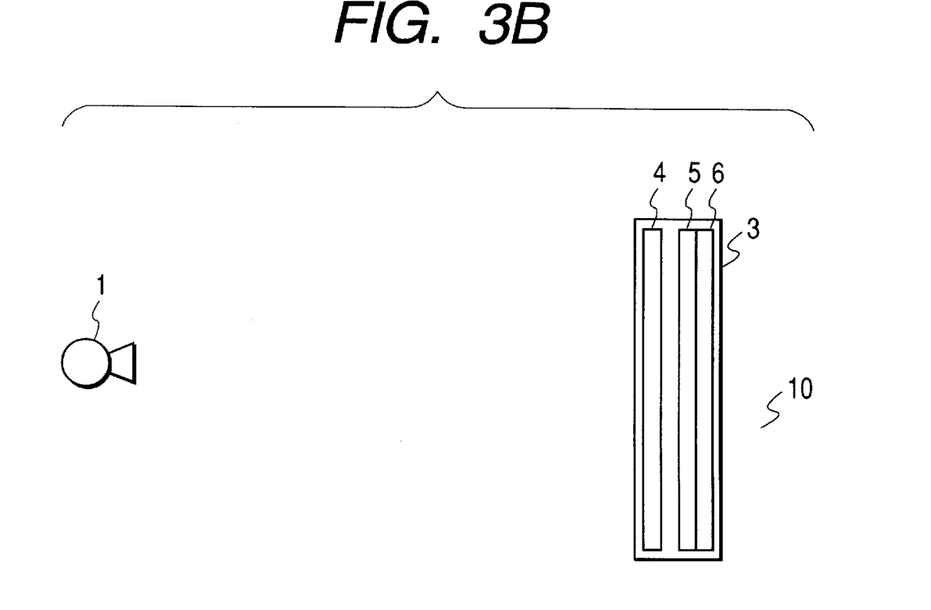
FIG. 3B illustrates a method of phototaking the image of the grid.

FIG. 2 is a typical structural diagram illustrating a radiographic apparatus according to a first embodiment of the present invention. FIGS. 3A and 3B are partial illustrations showing a state in which an object and a grid are absent in this apparatus and a state in which the grid is mounted and the object alone is absent, respectively.

In FIG. 2, the reference numeral 1 designates a radiation source for generating radiation, the reference numeral 2 denotes an object, the reference numeral 10 designates a radiographic unit, the reference numeral 3 denotes a housing having a window portion for passing the radiation therethrough and intercepting light so that the light may not enter the interior, the reference numeral 4 designates a grid for removing unnecessary scattered radiation created from the object 2, the reference numeral 5 denotes a fluorescent material for converting the radiation into fluorescence, and the reference numeral 6 designates a photoelectric conversion device formed of amorphous silicon and formed with a plurality of pixels comprising various semiconductor layers laminated and arranged in the form of a grid on one side of a transparent glass substrate having a thickness of several millimeters and having its both surfaces polished.

The reference numeral 11 denotes an A/D converter for effecting the A/D conversion of the output signal of the radiographic apparatus, the reference numeral 12 designates a controlling apparatus such as a CPU for controlling the operation of the entire radiographic system, the reference numeral 13 denotes a storing apparatus for temporarily storing a radiation image or the like therein, the reference numeral 14 designates an exterior storing apparatus such as an MOD for storing an image therein, the reference numeral 15 denotes a displaying apparatus such as a CRT display for displaying information, the reference numeral 16 designates an image processing apparatus for effecting an image calculating process, the reference numeral 17 denotes a radiation generating apparatus for driving the radiation source 1, and the reference numeral 18 designates a phototaking condition commanding apparatus such as a control panel for an operator to command a phototaking condition. These apparatuses are connected together through a bus line and form a network.

Description will first be made of the step of obtaining the radiation image of the grid. As shown in FIG. 3A, in a state in which the object 2 and the grid 4 are absent, a radiation generating signal is outputted from the controlling apparatus 12 to the radiation generating apparatus 17 to thereby generate radiation from the radiation source 1. The thus generated radiation is converted into fluorescence in the fluorescent material 5, and is detected as a radiation image analog signal which is a radiation intensity distribution i(x, y) by the photoelectric conversion device 6 ((x, y) are the coordinates of each pixel). This radiation image analog signal is converted into a digital signal by the A/D converter 11 and is transferred to the temporally storing apparatus 13. At the same time, it is transferred to the exterior storing apparatus 14 and is stored therein.

The digital signal obtained in the state in which the object 2 and the grid 4 are absent may be stored after being subjected to image processing suited for the image processing thereafter.

Subsequently, in a state in which as shown in FIG. 3B, the grid 4 is installed in the radiographic unit 10 and the object 2 is absent, the radiation image g(x, y) of the grid is likewise phototaken. The radiation image of the grid 4 (the image of the grid) g'(x, y) in which the radiation intensity distribution i(x, y) has been corrected is expressed as follows:

g'(x, y)=g(x, y)/i(x, y)

Further, in preparation for the image processing thereafter, the output of the phototaking condition commanding apparatus, i.e., a commanded phototaking condition, is also stored.

On the other hand, when the radiation intensity distribution i(x, y) can be regarded as being substantially uniform, when the radiation intensity distribution i(x, y) is known, or when the radiation intensity distribution i(x, y) substantially coincides with a radiation intensity distribution used for diagnosis, the step of phototaking the radiation intensity distribution i(x, y) can be omitted. In this case, g'(x, y) is handled as g'(x, y)=g(x, y). Also, in this case, it is more preferable that the phototaking of the radiation image g(x, y) or g'(x, y) of the grid 4 be effected during the running-in of a radiation tube.

The step of phototaking the object 2 will be explained hereinafter. As in the case where the image of the grid is obtained, a radiation generating signal is outputted from the controlling apparatus 12 to the radiation generating apparatus 17, thereby to generate radiation from the radiation source 1. The thus generated radiation is applied to the object 2, and is absorbed and scattered in conformity with the structure of the object, whereafter it arrives at the grid 4.

The grid 4 acts to remove unnecessary scattered radiation created from the object 2 and improve the contrast of the radiation image. In the fluorescent material 5, the radiation transmitted through the grid 4 is converted into fluorescence, and is detected as a radiation image analog signal in which the radiation image of the grid 4 is superposed on the radiation image of the object 2 by the photoelectric conversion device 6.

This radiation image analog signal is converted into a digital signal by the A/D converter 11 and is transferred to the temporarily storing apparatus 13. At the same time, it is transferred to the exterior storing apparatus 14 and is stored therein.

The digital signal obtained with the object phototaken may be stored after subjected to image processing suited for the image processing thereafter.

Description will now be made of the step of removing the image of the grid superposed on the radiation image of the object by image processing by the use of the radiation image of the grid and the radiation image of the object.

The grid has the function of selectively intercepting the radiation and therefore, the radiation image of the object 2 can be regarded as having been intensity-modulated by the grid 4. The intensity-modulated image can be restored to its original state if a function at which the intensity modulation has been effected is known. In the present embodiment, the function at which the intensity modulation has been effected is the radiation image g'(x, y) itself of the grid 4 and therefore, it becomes possible to utilize the radiation image of the grid 4 to remove the radiation image of the grid 4 superposed on the radiation image of the object 2.

An example of the image processing for removing the image of the grid will be described here. The radiation image of the object 2 on which the radiation image g'(x, y) of the grid 4 is superposed is defined as O(x, y), and the radiation image of the object 2 from which the radiation image g'(x, y) of the grid 4 has been removed is defined as O'(x, y).

The function at which intensity modulation has been effected on the radiation image of the object 2 is the radiation image g'(x, y) of the grid and assuming that the intensity modulation by g'(x, y) is effected by multiplication and division, the radiation image O'(x, y) of the object from which the radiation image of the grid 4 has been removed is obtained by image processing expressed by the following expression:

$$O'(x, y) = O(x, y)/g'(x, y)$$

Description will be made here of the step of image-processing the image of the grid on the basis of the output of the phototaking condition commanding means in order to cope with a case where the phototaking condition is changed, as when phototaking is effected with the distance between the radiation source 1 and the fluorescent material 5, i.e., the tube distance, changed, or when phototaking is effected with the tube voltage of the radiation source 1 changed.

First, when the tube distance is changed, generally the distance between the grid 4 and the fluorescent material 5 is not zero and therefore, enlargement or reduction occurs to the image of the grid superposed on the image O(x, y) of the object. So, prior to the removal of the image of the grid, the process of enlarging or reducing the function g'(x, y) of the image of the grid at a magnification corresponding to the amount of change in the tube distance is carried out to thereby carry out the image processing of making the magnifications of the stored image g'(x, y) of the grid and the image of the grid superposed on the image O(x, y) of the object coincident with each other.

Strictly explaining, however, the image of the grid is subjected to spatial frequency modulation by the image receiving means 6 and therefore, in some case, the enlargement or reduction rate of the image of the grid projected onto the image receiving means 6 differs from the enlargement or reduction rate of the image of the grid outputted by the image receiving means. In that case, the correction of an enlargement or reduction rate conforming to the sampling function of the image receiving means 6 becomes necessary.

Since the enlargement or reduction rate is not constant in the image field, the enlargement or reduction rate becomes non-linear in x and y directions and therefore, the correction of the enlargement or reduction rate sometimes becomes necessary. Generally, however, a focal length exists in the grid and the grid usually is not used at the other distances than the tube distance prescribed by the grid and the distance between the grid 4 and the fluorescent material 5 is minute and therefore, even if the enlargement or reduction rate is calculated as being linear, usually it is within a negligible range.

Description will now be made of a case where the tube voltage of the radiation source 1 is changed. Generally the grid is of structure in which radiation shielding substances and radiation transmitting substances are alternately arranged, but the radiation transmittances of the respective substances vary in conformity with the energy of the radiation and therefore, when the tube voltage of the radiation source 1 is changed, the control of the striped pattern of the image of the grid varies.

Then, the amplitude modulation or harmony processing of multiplying the image g'(x, y) of the grid by an intensity modulation function a(V) conforming to the tube voltage in conformity with the tube voltage is to effected, thereby to make it coincide with the intensity of the image of the grid superposed on the object. The intensity modulation function a(V) can be easily found by recording in advance a variation in the contract of the image of the grid for various tube voltages. Also, when phototaking conditions such as the tube correct and exposure time affect the image of the grid, the influence is likewise found in advance to thereby make it reflected in the image processing of the image of the grid.

Since part of the image processing described in the present embodiment is done by multiplication and division, the multiplication and division can be substituted for by addition and subtraction between logarithmic data after the logarithm of the data of each image has been taken. Also, it has been assumed that in the image processing described in the present embodiment, intensity modulation is done by multiplication and division, but the calculation effected by multiplication and division can also be substituted for by addition and substraction. Also, the radiation image of the grid 4 has been described as being obtained during the running-in of the radiation tube, but if the variation in the radiation image of the grid 4 with time is within a negligible range, a reduction in the frequency of the obtainment of the image is possible and therefore, in that case, no problem will arise except during the running-in.

A second embodiment of the present invention will now be described with reference to FIGS. 4 and 5.

This embodiment is a radiographic apparatus capable of removing the image of the grid highly accurately when changes in the phototaking condition during the phototaking of the image of the grid and the phototaking condition during the phototaking of the image of the object are unknown or even if the changes in the phototaking conditions are known. A typical structural diagram of the present embodiment is shown in FIG. 4, and a flow chart thereof is shown in FIG. 5.

Although partly overlapping, the members in FIG. 4 will hereinafter be described. In FIG. 4, the reference numeral 1 designates a radiation source for generating radiation, the reference numeral 2 denotes an object, the reference numeral 10 designates a radiographic unit, the reference numeral 3 denotes a housing having a window portion for passing the radiation therethrough and intercepting light so that the light may not enter the interior thereof, the reference numeral 4 designates a grid for removing unnecessary scattered radiation created from the object, the reference numeral 5 denotes a fluorescent material for converting the radiation into fluorescence, and the reference numeral 6 designates a photoelectric conversion device formed of amorphous silicon.

The reference numeral 11 denotes an A/D converter for effecting the A/D conversion of the output signal of the radiographic apparatus, the reference numeral 12 designates a controlling apparatus for controlling the operation of the entire radiographic system, the reference numeral 13 denotes a storing apparatus storing a radiation image or the like therein, the reference numeral 14 designates an exterior storing apparatus for storing an image therein, the reference numeral 15 denotes a displaying apparatus for displaying information, the reference numeral 16 designates an image processing apparatus for carrying out an image calculating process, the reference numeral 17 denotes a radiation generating apparatus for driving the radiation source 1, the reference numeral 18 designates a phototaking condition commanding apparatus for commanding a phototaking condition, and the reference numeral 19 denotes an image evaluating apparatus.

A method of removing the image of the grid according to the second embodiment will now be described with reference to FIG. 5. In the ensuing description, steps similar to those in the first embodiment will be omitted.

As in the first embodiment, the step of phototaking the image of the grid and the step of phototaking the image of the object are executed. Next, the step of image-processing the image of the grid is executed.

In the step of processing the image of the grid, image processing is effected in conformity with the output of the phototaking condition commanding apparatus when there is such output, but when there is not the output of the phototaking condition commanding apparatus, predetermined image processing is effected or image processing is not effected. This grid image is called the primary grid image. Subsequently, the step of removing the grid image superposed on the object image by image processing by the use of the primary grid image and the object image is executed. The output image at this time is called the primary image. This primary image is in some case not subjected to the optimum grid image removing process, and in such case, the grid image (error grid image) which could not be completely removed is superposed on the object image. This primary image is inputted to the image evaluating apparatus 19 to thereby effect the evaluation of the error grid image and find the amount of error to be cancelled.

The step of finding the amount of error to be cancelled will be described here. The image evaluating apparatus 19 has the image processing function and the image evaluating function, and uses these functions to effect the analysis of the error grid image superposed on the object image.

Generally the error grid image is high in spatial frequency and periodic as compared with the object image and therefore, in the image evaluating apparatus 19, suitable filter processing is effected, whereby the error grid image can be easily extracted.

The main feature of the error grid image is classified into the following three points. The first point is the Moire striped pattern by the error of the enlargement or reduction rate, and the amount of the error of the enlargement or reduction rate can be found from the analysis of the period of the Moire stripes.

The second point is the striped pattern by the error of the contrast, and the phase of the striped pattern is characterized in that it coincides with or is reversed from the primary grid image. The absolute value of the error of the contrast can be found from the magnitude of the contrast of the error grid image, and the positive or negative sign of the error of the contrast can be found from the presence or absence of the reversal of the phase.

The third feature is that it is the striped pattern by the error of lateral displacement and the phase of the striped pattern does not coincide with the primary grid image. From this amount of phase, the amount of displacement error can be found. By the primary image being thus inputted to the image evaluating apparatus, the amount of error to be cancelled by the grid image removing process is found.

Next, the amount of error to be cancelled outputted by the image evaluating apparatus 19 is fed back to the image processing apparatus 16, and the image processing condition is changed in conformity with the amount of error to be cancelled and the grid image processing is effected again. The modified grid image obtained here is called the secondary grid image. The secondary grid image has the amount of error to be cancelled reflected therein and therefore, even if the phototaking condition for the object image is unknown, the secondary grid image in principle coincides with the grid image superposed on the object image.

Subsequently, the grid image removing image processing is effected again. Thereby it becomes possible to obtain an object image from which the grid image has been removed well.

Also, if necessary, it is also possible to further input the obtained object image to the image evaluating apparatus, and repeat processing until the amount of error to be cancelled reaches a predetermined range. In this case, if the amount of error to be cancelled by the grid image removing process does not converge within a predetermined range, instructions for displaying are sent to the displaying means so that the grid image may be phototaken again.

Now, the step of obtaining the primary grid image to the step of finding the final amount of error to be cancelled do not always require the information of the entire image field. The reason for this is that the grid image is a striped pattern and is considered to be substantially uniform in a direction parallel to the stripes. Therefore it is also possible to evaluate only pixels in a representative row to thereby find the amount of error to be cancelled. In this case, only the pixels in a row are evaluated and therefore the time required for image processing can be greatly curtailed. However, it is also possible to evaluate pixels in a plurality of rows to improve the accuracy of calculation. Also, the evaluation of pixels in a plurality of rows differing in position from one another is effective when a rotational component is to be found.

As described above, the radiographic apparatus according to the present embodiment is capable of effecting high-speed and good grid removal image processing even if the pre-stored grid image is one and the object image phototaking condition is unknown.

A third embodiment of the present invention which will hereinafter be described makes the contrast of a pre-stored grid image highly accurately resemble the contrast of a grid image superposed on the object image to thereby effect highly accurate removal of the grid image.

A grid phototaking method according to the present embodiment will now be described with reference to FIG. 6. Generally the object has the action of scattering radiation and therefore, the contrast of the grid image when the object is present is reduced due to the influence of scattered radiation, as compared with the contract of the grid image when the object is absent. Accordingly, during the grid image phototaking effected in advance, a scattered ray generating member having a scattered ray characteristic equal to that of the object is provided at the object position, whereby it becomes possible to effect the phototaking of a grid image resembling the grid image superposed on the object image.

Figure 6:
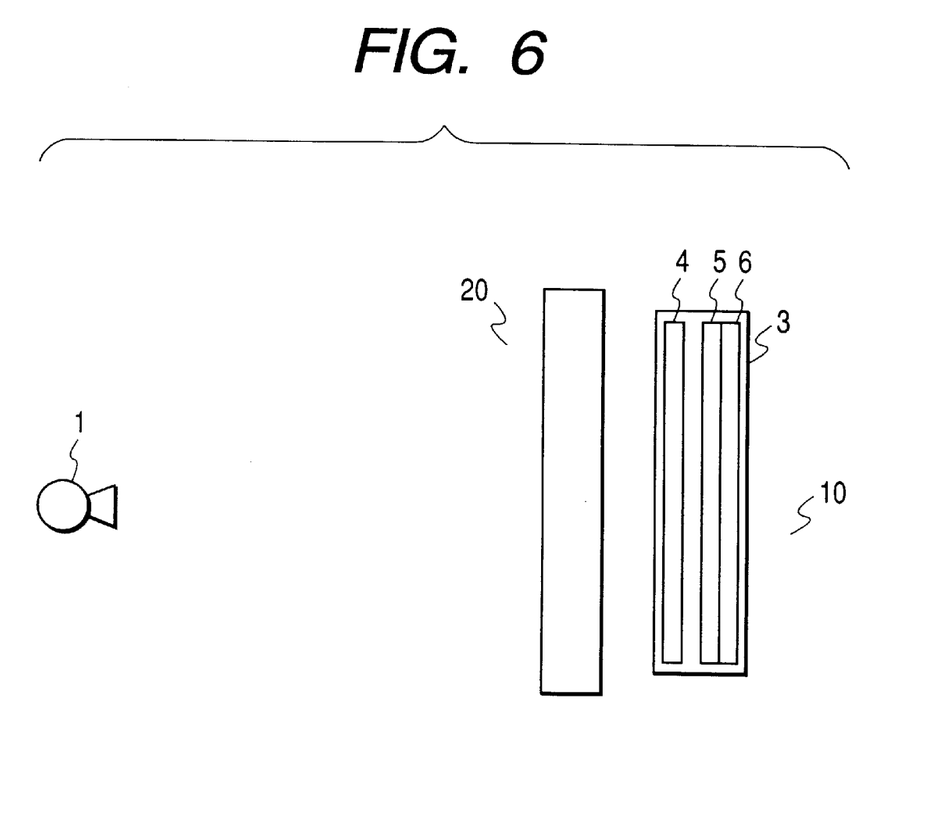
FIG. 6 illustrates a method of phototaking the image of the grid by the use of a scattered ray generating member.

In FIG. 6, the reference numeral 20 designates a scattered ray generating member which, when the object is a human body, can utilize a water phantom comprising an acryl plate or an acryl box having a uniform thickness and filled with water.

The radiation generated from the radiation source 1 acts on the scattered ray generating member 20 and the phenomena of absorption, scattering and transmission occur. The scattered ray generating member 20 has the characteristic of spatially uniformly transmitting radiation therethrough and therefore, the radiation arriving at the grid 4 is radiation uniform in intensity but including scattered rays.

The scattered rays which have arrived at the grid can hardly pass through the grid because of the scattered ray removing function which is the original function of the grid, but part of them passes through the grid and irradiates the fluorescent material 5, thereby reducing the contrast of the grid image arriving at the image receiving means 6. This grid image resembles the contrast of a grid image formed by radiation transmitted through a human body which is the scattered ray generating member, and therefore, by storing this grid image and utilizing it in the grid image removing process, a highly accurate grid image removing process becomes possible.

Also, as in the first embodiment and the second embodiment, these grid images are image processed, whereby it is possible to effect more highly accurate grid image removal.

The aforementioned pre-stored grid image need not always be an actually phototaken grid image. When this grid image can be expected, it can be substituted for by an imaginary grid image made by a computer. Of course, at this time, with the effect of scattered rays taken into account, the contrast of the aforementioned imaginary grid image can be suitably set.

In the above-described embodiments, the means for detecting radiation has been described as being a fluorescent material and a photoelectric conversion device, but the present invention is effective in removing a grid image in a radiographic apparatus using a grid to phototake an object, and is particularly effective in a radiographic apparatus in which a radiation image is discretely sampled and detected. The present invention is not restricted to the embodiments shown by way of example, but is also applicable, for example, to a radiographic apparatus in which use is made of an accumulative accelerated fluorescent material excited by radiation to discretely sample accelerated fluorescence. It can also be applied to a radiographic apparatus using a radiation detecting apparatus such as amorphous selenium, CdTe or an ion chamber, using a radiation-electron converting member for converting radiation into electrons and an electron detecting device for discretely sampling the generated electrons.

As described above, a grid image superposed on the radiation image of the object is expected and removed from a first grid image obtained in a state in which the object is absent and therefore, it becomes possible to obtain a radiation image from which the grid image has been effectively and accurately removed.

What is claimed is:

1. A radiographic apparatus for obtaining the radiation image of an object, comprising:
    a phototaking unit including a grid, being capable of obtaining radiation image data including grid pattern; and
    a processor effecting image processing to remove the grid pattern superimposed on the radiation image data obtained by said phototaking unit, the processor executing division process to divide said radiation image data by predetermined grid image data at each pixel,
    wherein said predetermined grid image data can be modified by said processor to make said predetermined grid image data resemble grid image data superimposed on the radiation image data.

2. An apparatus according to claim 1, wherein said processor executes the following division calculations at each pixel:

$$O'(x,y)=O(x,y)/g'(x,y)$$

where $O(x,y)$ denotes the radiation image data, $g'(x,y)$ denotes the predetermined grid image data, and $O'(x,y)$ denotes radiation image data which have been processed by said processor.

3. An apparatus according to claim 1, wherein said predetermined grid image data is obtained by modifying grid image data actually phototaken without the object, with modification based on a phototaking condition on said radiation image data.

4. An apparatus according to claim 1, wherein said predetermined grid image data is radiation image data obtained by the actual phototaking of a scattered ray generating member instead of the object.

5. An apparatus according to claim 1, wherein said predetermined grid image data is imaginary grid image data made by a computer.

6. An apparatus according to claim 1, wherein said processor executes suitable image processing based on a phototaking condition on said radiation image data.

7. An apparatus according to claim 3, wherein said phototaking condition has at least one of a distance between a tube as a radiation source and the phototaking unit used in phototaking, a tube voltage, a tube current and exposure time.

8. An apparatus according to claim 1, wherein said processor evaluates a removal error that has occurred when said removal processing has been executed by the use of said predetermined grid image data, and modifies said predetermined grid image data on the basis of the result of said evaluation.

9. An apparatus according to claim 8, wherein said error to be evaluated has at least one of errors of enlargement or reduction rate, contrast, lateral displacement and rotation.

10. An apparatus according to claim 1, wherein said phototaking unit includes a detector and a converter for converting radiation into a medium detectable by said detector.

11. An apparatus according to claim 1, wherein said phototaking unit has a photoelectric element, and a converter for converting radiation into light detectable by said photoelectric element.

12. An apparatus according to claim 11, wherein said photoelectric element has an amorphous silicon sensor.

13. An apparatus according to claim 11, wherein said converter has a fluorescent material.

14. An apparatus according to claim 1, wherein said phototaking unit has an electron detector, and a convertor for converting radiation into electrons.

15. A radiographic method for obtaining a radiation image of an object, comprising the steps of:
    obtaining radiation image data through a grid; and
    effecting image processing to remove grid pattern superimposed on the radiation image data, by division processing to divide the radiation image data with the object by predetermined grid image data at each pixel,
    wherein said predetermined grid image data can be modified to make said predetermined grid image data resemble grid image data superimposed on the radiation image data.

16. A method according to claim 15, wherein said predetermined grid image data is obtained by modifying grid image data actually phototaken without the object, with said modification based on a phototaking condition on said radiation image data.

17. A method according to claim 15, wherein the predetermined grid image data is obtained by effecting radiation image phototaking of a scattered ray generating member instead of the object through the grid.

18. A method according to claim 15, wherein the predetermined grid image data is imaginary grid image data made by a computer.

19. A method according to claim 15, wherein said modification is effected according to an inputted phototaking condition on said radiation image data of said object obtained through the grid.

20. A method according to claim 15, further comprising the steps of:
   finding a grid pattern removal error in said radiation image data with the object on which said image processing has been effected;
   making modified grid image data on the basis of said error; and
   dividing the radiation image data with the object by said modified predetermined grid image data at each pixel.

21. A method according to claim 20, wherein said error to be found has at least one of errors of enlargement or reduction rate, contrast, lateral displacement and rotation.

22. A method according to claim 20, wherein with said error as a first grid pattern removal error and N as 2 or a greater natural number, the step of finding an Nth grid pattern removal error in said radiation image data of said object on which said image processing has been effected on the basis of the N-1th grid pattern removal error, the step of re-modifying, on the basis of said Nth error, the predetermined grid image data having been obtained on the basis of an N-1th error, and the step of dividing the radiation image data with the object by the predetermined grid image data having been obtained on the basis of said Nth error at each pixel are repeated.

23. A method according to claim 22, wherein warning is effected when an Mth error does not converge within a prescribed range, where M is 2 or a greater natural number.

24. A radiographic method for obtaining a radiation image of an object, comprising the steps of:
   obtaining radiation image data through a grid in a state in which the object is absent;
   image-processing the radiation image data obtained through the grid in the state in which the object is absent to thereby obtain the data of the expected image of the grid during the presence of the object;
   obtaining the radiation image data of the object through the grid; and
   removing the data of the expected image of the grid from the radiation image data of the object,
   wherein the radiation image data obtained through the grid in the state in which said object is absent is imaginary radiation image data made by a computer.

25. A radiographic apparatus for obtaining the radiation image of an object, comprising:
   a phototaking unit including a grid, being capable of obtaining radiation image data including a grid pattern;
   a processor effecting image processing to remove the grid pattern superimposed on the radiation image data obtained by said phototaking unit, the processor executing a division process to divide said radiation image data by predetermined grid image data at each pixel,
   wherein said predetermined grid image data is radiation image data obtained by the actual phototaking of a scattered ray generating member instead of the object.

26. A radiographic method for obtaining a radiation image of an object, comprising the steps of:
   obtaining radiation image data through a grid; and
   effecting image processing to remove a grid pattern superimposed on the radiation image data, by division process to divide the radiation image data with the object by predetermined grid image data at each pixel,
   wherein the predetermined grid image data is obtained by effecting radiation image phototaking of a scattered ray generating member instead of the object through the grid.

* * * * *

UNITED STATES PATENT AND TRADEMARK OFFICE
CERTIFICATE OF CORRECTION

PATENT NO. : 6,285,781 B1
DATED : September 4, 2001
INVENTOR(S) : Tatsuya Yamazaki It is certified that error appears in the above-identified patent and that said Letters Patent is hereby corrected as shown below:

Title page,
Item [56], References Cited, OTHER PUBLICATIONS, "mammography"By" should read -- mammography" by --.

Figure 4:
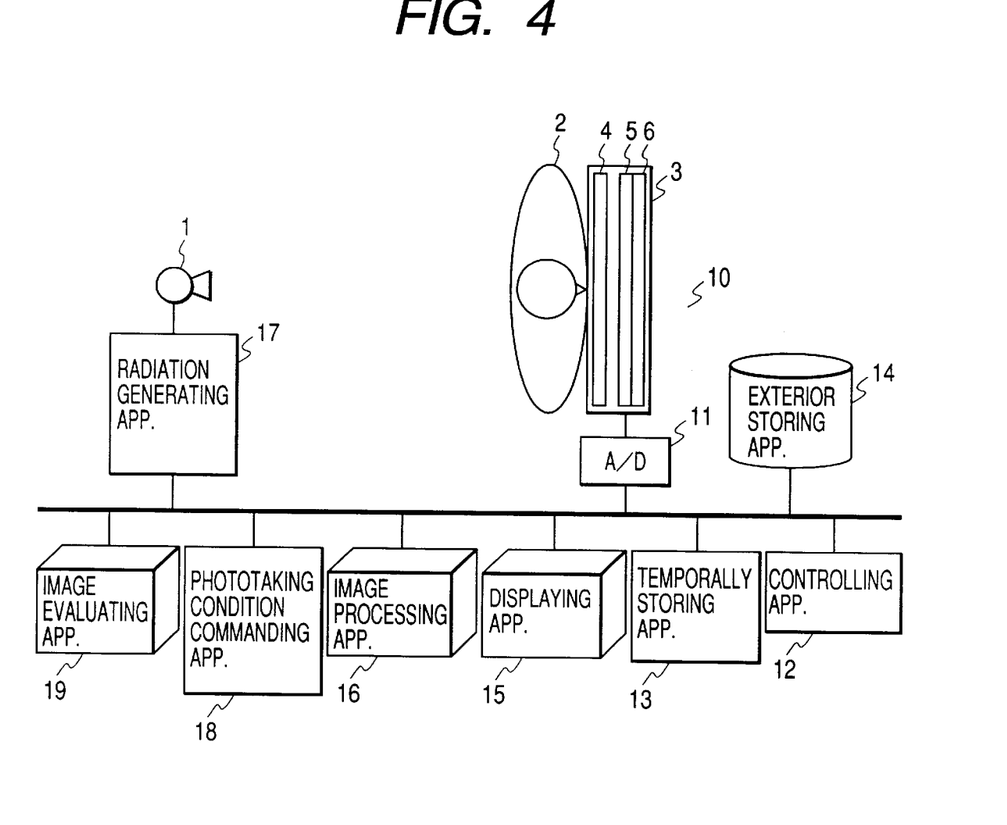
FIG. 4 illustrates a radiographic apparatus according to a second embodiment of the present invention.
Figure 5:
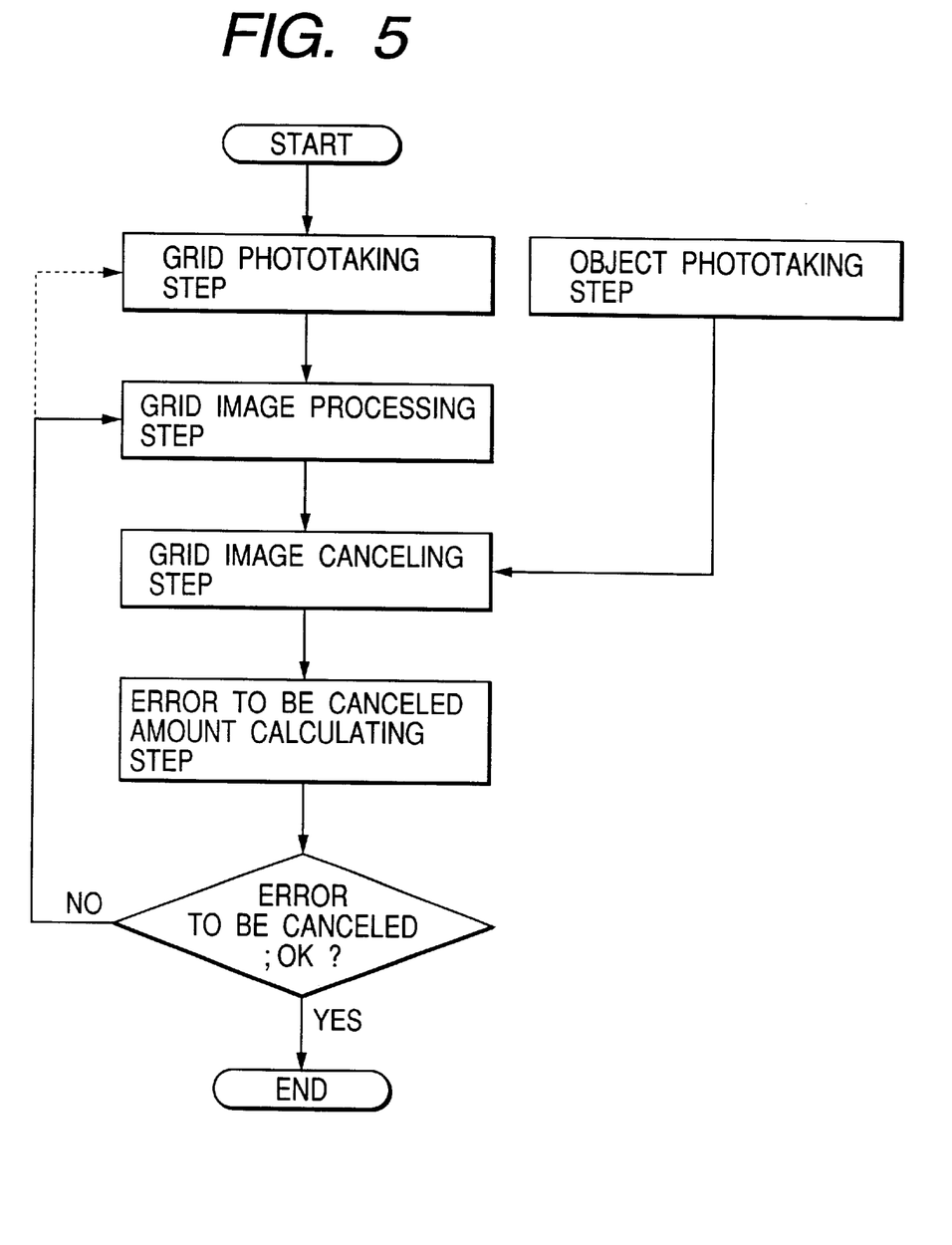
FIG. 5 is a flow chart illustrating the concept of the second embodiment.

Drawing,
Sheet 2, Figure 2, "TEMPORALLY" should read -- TEMPORARILY --; and
Sheet 4, Figure 4, "TEMPORALLY" should read -- TEMPORARILY --.

Column 1,
Line 33, "film" should read -- film, --; and
Line 41, "IP," should read -- "IP", --.

Column 2,
Line 21, "selected," should read -- selected --;
Line 22, "to" should be deleted;
Line 24, "is reduced" should be deleted;
Line 25, "grid," should read -- grid is reduced, --; and
Line 40, "Moire" should read -- Moiré --.

Column 3,
Line 65, "temporally" should read -- temporarily --.

Column 5,
Line 38, "case," should read -- cases, --.

Column 6,
Line 5, "contract" should read -- contrast --; and
Line 8, "to thereby" should read -- thereby to --.

Column 7,
Line 19, "case" should read -- cases --;
Line 37, "Moire" should read -- Moiré --;
Line 40, "Moire" should read -- Moiré --;
Line 50, "that it is" should be deleted; and
Line 52, "does" should read -- do --.

Column 9,
Line 46, "pattern;" should read -- patterns; --; and
Line 49, "pattern" should read -- patterns --.

UNITED STATES PATENT AND TRADEMARK OFFICE
CERTIFICATE OF CORRECTION

PATENT NO. : 6,285,781 B1
DATED : September 4, 2001
INVENTOR(S) : Tatsuya Yamazaki It is certified that error appears in the above-identified patent and that said Letters Patent is hereby corrected as shown below:

Column 10,
Line 42, "convertor" should read -- converter --; and
Line 47, "pattern" should read -- patterns --.

Column 11,
Line 22, "the N-1 th" should read -- an N-1th --; and
Line 25, "an N-1th" should read -- the N-1th --.

Column 12,
Line 14, "pattern;" should read -- pattern; and --.

Signed and Sealed this

Twenty-third Day of April, 2002

Attest:

JAMES E. ROGAN
Attesting Officer     Director of the United States Patent and Trademark Office